United States Patent
Imhof-Röthlin et al.

(10) Patent No.: US 8,845,650 B2
(45) Date of Patent: Sep. 30, 2014

(54) INSTRUMENT FOR HANDLING A JOINT COMPONENT BY WAY OF A VACUUM

(75) Inventors: Martin Imhof-Röthlin, Meggen (CH); René Brack, Auenstein (CH)

(73) Assignee: Smith & Nephew Orthopaedics AG, Baar (CH)

( * ) Notice: Subject to any disclaimer, the term of this patent is extended or adjusted under 35 U.S.C. 154(b) by 643 days.

(21) Appl. No.: 13/121,737

(22) PCT Filed: Sep. 24, 2009

(86) PCT No.: PCT/EP2009/062394
§ 371 (c)(1),
(2), (4) Date: Oct. 14, 2011

(87) PCT Pub. No.: WO2010/037685
PCT Pub. Date: Apr. 8, 2010

(65) Prior Publication Data
US 2012/0029524 A1 Feb. 2, 2012

(30) Foreign Application Priority Data
Sep. 30, 2008 (DE) .......... 10 2008 049 661

(51) Int. Cl.
A61B 17/56 (2006.01)
A61F 2/46 (2006.01)
A61F 2/30 (2006.01)

(52) U.S. Cl.
CPC ....... *A61F 2/4609* (2013.01); *A61F 2002/4685* (2013.01); *A61F 2/4612* (2013.01); *A61F 2002/30069* (2013.01); *A61F 2002/30616* (2013.01)
USPC .......... 606/99

(58) Field of Classification Search
USPC .......... 606/81, 91, 99; 294/183–189
See application file for complete search history.

(56) References Cited

U.S. PATENT DOCUMENTS

| | | | | |
|---|---|---|---|---|
| 6,152,930 | A * | 11/2000 | Mastrorio | 606/99 |
| 7,927,376 | B2 * | 4/2011 | Leisinger et al. | 623/23.43 |
| 2002/0175527 | A1 * | 11/2002 | Huang | 294/64.1 |
| 2005/0137603 | A1 * | 6/2005 | Belew et al. | 606/91 |
| 2007/0225725 | A1 | 9/2007 | Heavener et al. | |

FOREIGN PATENT DOCUMENTS

| | | |
|---|---|---|
| DE | 197 04 577 A1 | 8/1998 |
| DE | 101 28 234 A1 | 1/2003 |
| FR | 2 877 210 | 5/2006 |
| WO | WO 2007/025639 A1 | 3/2007 |

OTHER PUBLICATIONS

Written Opinion and International Search Report from International Application No. PCT/EP2009/062394.

* cited by examiner

*Primary Examiner* — Christopher Beccia
(74) *Attorney, Agent, or Firm* — Ropes & Gray LLP

(57) ABSTRACT

Setting instrument (10) for a hip socket or shoulder socket inlay, having a handle part (11) and a suction element (12) that can be brought into sealing contact with the joint surface. The suction element (12) comprises a flexible molded part (13) matched to the joint surface, which molded part is deformable by a pulling element (14) in such a way that, when applied to the joint surface, an (increased) partial vacuum is formed between the joint surface and the flexible molded part (13).

18 Claims, 3 Drawing Sheets

INSTRUMENT FOR HANDLING A JOINT COMPONENT BY WAY OF A VACUUM

Figure 1:
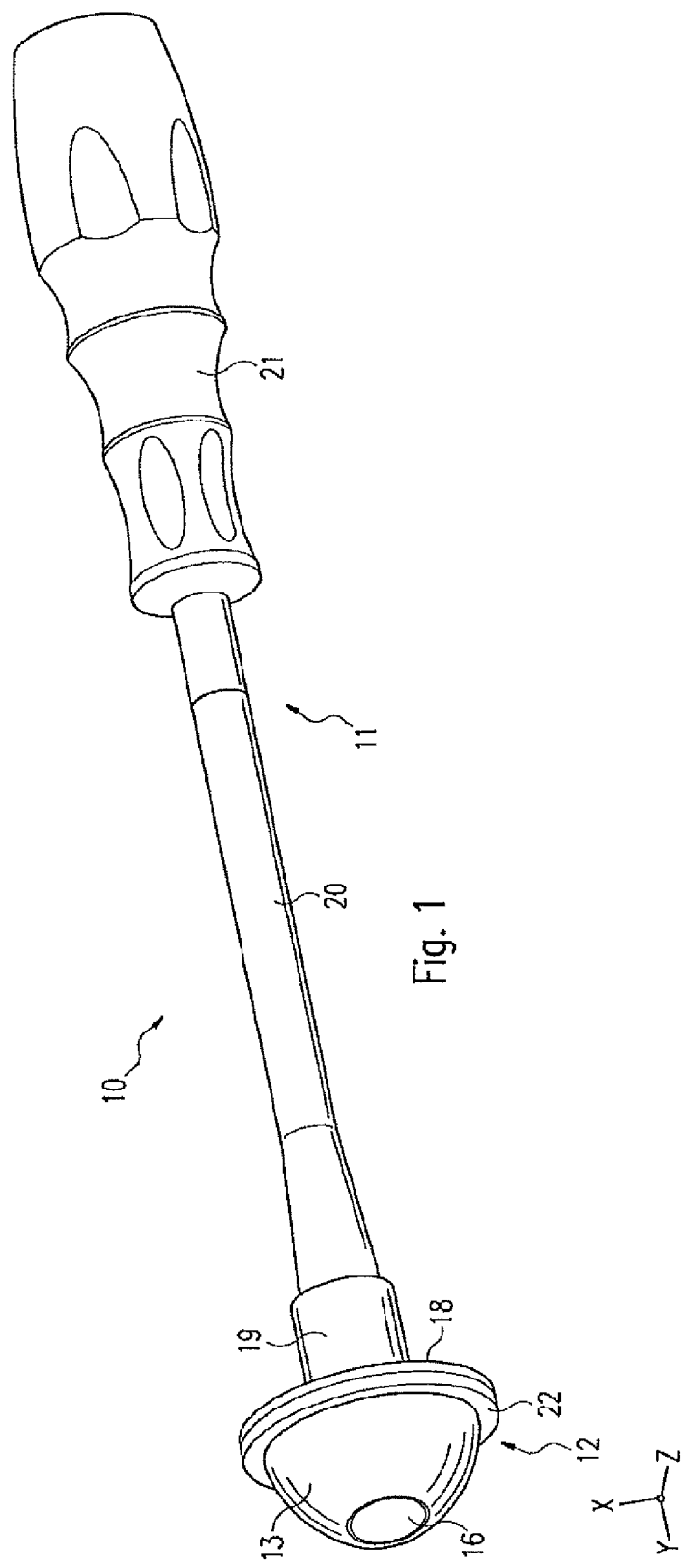

This application is a United States National Phase filing of International Application No. PCT/EP2009/062394 filed on Sep. 24, 2009 which claims the benefit of DE 102008049661.8 filed on Sep. 30, 2008, both of which are herein incorporated by reference.

The present invention relates to an instrument for handling a joint component of a joint prosthesis, which joint component comprises a joint surface, especially a concave joint surface, especially a setting instrument for a hip socket or shoulder socket inlay, having a handle part and a suction element that can be brought into sealing contact with the joint surface.

Such instruments are generally known. In this respect reference is made merely by way of example to DE 197 04 577 A1, DE. 101 28 234 A1 and WO 2007/025639 A1.

All of those known setting instruments have in common a suction element in the form of a suction cup. Such setting instruments have been thoroughly proven in practice, but they are relatively complicated in terms of their handling and also have only a limited degree of operational reliability. In addition, in the case of the prior art according to both DE 101 28 234 A1 and DE 197 22 923 A1, two-handed operation is mandatory. In each case there is also a risk that the partial vacuum in the suction space between the suction cup and the joint surface will be unintentionally released, with the result that the joint component will fall from the instrument at an inconvenient moment. The reason for this, for example in the case of the setting instrument according to DE 101 28 234 A1, is primarily that the actuating element for the pressure-release valve projects axially rearwards beyond the handle surface, that is to say in the direction towards the user. Accordingly, it cannot be ruled out that, when the instrument is gripped, the actuating element for the pressure-release valve will inadvertently be touched and unintentionally actuated.

Starting from the mentioned prior art, the present invention is therefore based on the problem of providing an instrument of the kind mentioned at the beginning which provides one-handed operation and a high degree of operational reliability and which, in particular, can also be used intra-operatively.

That problem is solved according to the invention by the characterizing features of claim 1, advantageous developments and structural details being described, in the subsidiary claims.

The present invention relates also to an arrangement for a setting instrument of the kind in question herein in accordance with claim 15. In practice, joint components of different sizes are used. To accommodate those different sizes, according to the invention a set of differently sized flexible moulded parts is to be provided, the setting instrument otherwise not requiring any modification.

The instrument according to the invention is based on the partial vacuum principle. It comprises a suction element having a flexible moulded part matched to the joint surface, which moulded part has a portion the surface of which corresponds as exactly as possible to the associated joint surface. Accordingly, as soon as the suction element and the joint surface are put together, a not insignificant vacuum is formed. That vacuum needs to be intensified, however. For that purpose, there is associated with the flexible moulded part a pulling element by means of which the flexible moulded part is to be deformable in such a way that, when applied to the joint surface, the partial vacuum between the joint surface and the moulded part is increased. By means of the pulling element, the moulded part is to be deformed inwards into the moulded part at the location at which the pulling element acts.

As a result, the instrument is correctly drawn into the implant. At the same time, the region around the point at which the pulling element acts undergoes radial expansion, so that increased sealing between the flexible moulded part and the joint surface is obtained. As a result, overall a high degree of operational reliability in the handling of the instrument according to the invention is achieved. There is no risk of the joint component's inadvertently falling from the setting instrument. The instrument according to the invention can also be used very satisfactorily for exact navigation of the implant. By virtue of the high degree of attachment between the joint component and the instrument, the latter is also suitable for intra-operative handling, that is to say removal of the joint component and re-alignment thereof during the operation. The instrument according to the invention is especially suitable for handling a cemented socket or a socket insert made of polyethylene, metal or ceramics, that is to say as a setting instrument for a hip socket or shoulder socket inlay.

The flexible moulded part is preferably made of silicone.

In a preferred embodiment, a pulling screw having a threaded shank and a screw head has proved suitable as pulling element; in the case of the hemispherical suction portion of the flexible moulded part, the screw head is then preferably associated with the pole of the hemispherical suction portion. The threaded shank of the pulling screw is arranged to be screwed into the distal end of the rod-like handle part, the flexible moulded part then being clamped between the screw head and the handle part, or rather a support surface arranged at the distal end thereof.

The pulling screw can also be coupled to an actuating means on the handle part by way of a length of wire cord or a thin rod, it being possible for the actuating means to comprise, for example, an eccentric.

Alternatively, it is also conceivable for the pulling force to be applied to the flexible moulded part by an external suction device. In that case the pulling element used is, for example, a plunger displaceably mounted at the distal end of the handle part, which plunger can be drawn inwards by means of a line passing through the handle part, with the flexible moulded part being drawn in and deformed accordingly.

Figure 2:
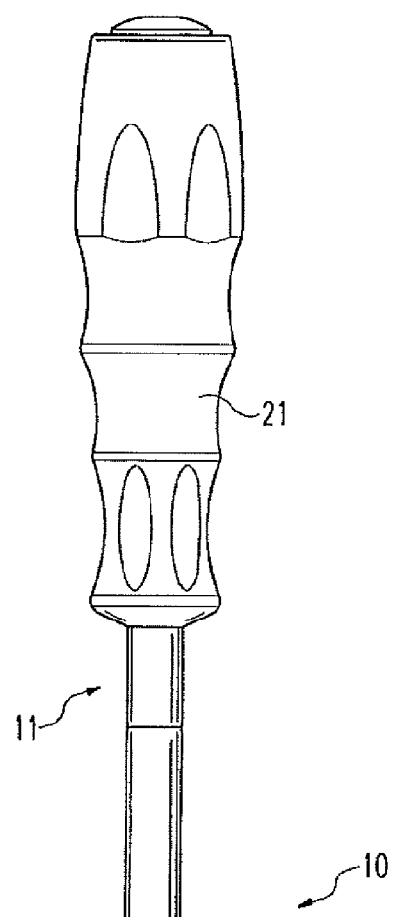
Figure 3:
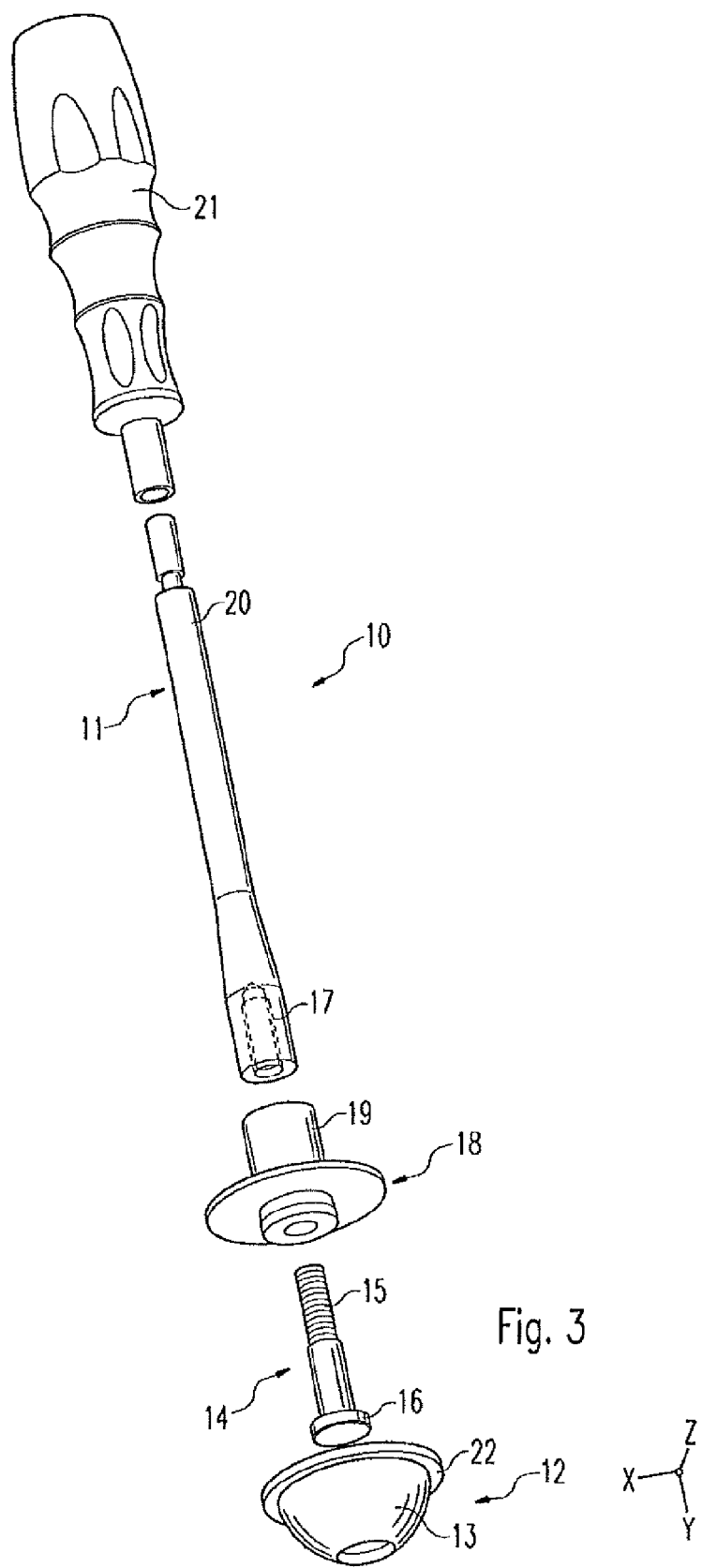

Hereinbelow, however, an especially preferred, structurally simple and very operationally reliable embodiment of a setting instrument according to the invention will be described in detail with reference to the accompanying drawing, wherein FIG. 1 is a perspective view of an embodiment of a setting instrument according to the invention;

FIG. 2 is a side view, but partly in section, of the setting instrument according to FIG. 1; and FIG. 3 is an exploded perspective view of the setting instrument according to FIGS. 1 and 2.

FIGS. 1 to 3 show a setting instrument for a hip socket or shoulder socket inlay, referred to hereinbelow only as a setting instrument, having a handle part 11 and a suction element 12 which can be brought into sealing contact with the joint surface of a joint prosthesis, for example a socket (not shown herein). The suction element 12 comprises a flexible moulded part 13 matched to the joint surface, which moulded part is preferably made of silicone or the like, and which is deformable by a pulling element in the form of a pulling screw 14 in such a way that, when applied to the joint surface, a partial vacuum is formed between the joint surface and the flexible moulded part 13. The pulling element in the form of the pulling screw 14 is manipulable from the handle part 11, as will be described in further detail below. The flexible moulded part 13 comprises a hemispherical suction portion corresponding to a concave joint surface of a hip socket or shoulder socket inlay made of polyethylene, ceramics or metal.

The pulling screw 14 has a threaded shank 15 and a screw head 16. Where the suction portion of the flexible moulded part 13 is of hemispherical form, the screw head 16 is associated with the pole thereof, as can be seen especially well in FIG. 1.

The threaded shank 15 of the pulling screw 14, as FIGS. 2 and 3 very clearly show, is arranged to be screwed into the distal end of the handle part 11. The internal thread provided at the distal end of the handle part 11 is indicated by reference numeral 17 in FIG. 3. The threaded shank 15 of the mentioned pulling screw 14 is arranged to be screwed into that internal thread. In this case, the flexible moulded part 13 is then clamped between the screw head 16 and the handle part or rather a support surface arranged at the distal end thereof. In the embodiment shown, the support surface is defined by a support flange 18. The support flange 18 is mountable as a separate component on the distal end of the handle part 11. For that purpose, the support flange 18 comprises a mounting sleeve 19, into which the distal end of the handle part 11 is inserted. The proper association between the handle part 11 and the support flange 18 including the mounting sleeve 19 is ensured by the pulling screw 14.

The pulling screw 14, which passes axially through the flexible moulded part 13 when the setting instrument 10 is in the assembled state, is non-rotatably secured inside the flexible moulded part 13. As a result, by rotation of the handle part 11 inside the mounting sleeve 19 relative to the latter, to the support flange and thus also to the suction element 12, i.e. the flexible moulded part 13, it is possible for the pulling screw 14 to be screwed to a greater or lesser extent into the distal end of the handle part 11, i.e. into the internal thread 17 provided therein, with the result that the screw head 16 also draws the flexible moulded part 13 inwards to a greater or lesser extent in its pole region. As a result, the partial vacuum in the pole region of the flexible moulded part 13 between the moulded part and the associated joint surface is increased. At the same time, as a result of that inward deformation in the pole region, the flexible moulded part is pushed outwards at a distance from the pole region, with the result that the flexible moulded part 13 and the joint surface are additionally pressed against one another. Such additional pressing increases the sealing action between the flexible moulded part 13 and the joint surface and also additionally secures the flexible moulded part 13 and the joint surface against relative rotation.

As can very clearly be seen in FIGS. 1 to 3, the handle part 11 has a rod-like portion 20 against the distal end of which the flexible moulded part 13 is supported and the proximal end of which comprises a handgrip 21. The handgrip is constructed in a similar way to a screwdriver handle. The rod-like portion 20 of the handle part 11 is of rigid construction in the embodiment shown, but it can also be resiliently flexible, at least in some regions, for example in a similar way to a flexible drive shaft. The degree of freedom for the surgeon is thus additionally increased. It is, of course, necessary to ensure that turning moments are transmitted to the pulling screw.

Furthermore, FIGS. 1 to 3 clearly show that the flexible moulded part 13 has a peripheral rim 22 extending equatorially and radially outwards. The peripheral rim enables the flexible moulded part 13 to be supported on the corresponding peripheral rim of a socket, especially of a socket inlay. In addition, it secures the flexible moulded part 13 and the joint component against relative rotation, especially immediately after the as yet undeformed suction element 12, i.e. the flexible moulded part 13, has been inserted into the joint component.

As already mentioned above, at the distal end of the handle part 11, more specifically at the distal end of its rod-like portion 20, there is arranged a support flange 18 against which the flexible moulded part 13 is supportable. The support flange 18 extends over the entire proximal surface of the flexible moulded part 13, i.e. the surface thereof facing the handle part 11, that is to say also over the mentioned peripheral rim 22. The peripheral rim 22 is therefore likewise supported.

The non-rotatable anchoring of the pulling screw 14 inside the flexible moulded part 13 can otherwise also be obtained by the pulling screw 14 being cast in the flexible moulded part 13, in the case of a modular construction, the shank between the thread and the screw head preferably has an angular or elliptical cross-section which matches a corresponding cross-section of an axial opening through the flexible moulded part.

Steps are also taken in this respect so that the flexible moulded part 13 is held secure against rotation relative to the support flange 18, so that when the handle part 11 is rotated about its longitudinal axis it is rotatable only relative to the two afore-mentioned parts 13, 18 and relative to the pulling screw 14. In this case, the mounting sleeve 19 therefore serves purely as a guide sleeve for the distal end of the handle part 11.

The flexible moulded part 13, the support flange 18, including the mounting or guiding sleeve 19, and the handle part 11 are held together by the pulling screw 14. If the handgrip 21 is further rotated, so that the pulling screw 14, going beyond its purely holding function, is additionally moved into the moulded part 13, the flexible moulded part is drawn inwards in the region of the screw head. The height of the flexible moulded part 13 is thus reduced. As a result, a corresponding cavity is formed between the flexible moulded part 13 and the associated joint surface. An increased partial vacuum is built up in that cavity, which generates a secure hold between the setting instrument 10 and the joint component. The peripheral rim 22 serves on the one hand for additional sealing with respect to the joint component, but on the other hand prevents the joint component from being tilted by the setting instrument 10. The tilt stability is increased by the support flange 18 which also extends over the peripheral rim 22.

It should also be pointed out that the described setting instrument does not have any parts that project laterally beyond the joint component being handled, for example the socket or inlay. It is very slim in the region of the field of operation and also does not obstruct the surgeon's view. The mentioned peripheral rim 22, including the associated support flange 18, prevents tilting. The implant can accordingly be inserted with precise axial alignment. The degree of attachment between the joint component and the instrument is very high. The instrument can be removed and re-attached again intra-operatively. As a result of the axial stability it is also possible to attach a device for socket navigation to the instrument. In particular, the described instrument also allows one-handed operation.

Also of importance is an arrangement for an instrument 10 consisting of a
- set of flexible moulded parts 13 of different sizes corresponding to joint surfaces or joint components of different sizes, a
- handle part 11 common to the set of differently sized moulded parts 13 and a pulling element, namely a pulling screw 14, and optionally a
- set of support flanges 18 matched to the differently sized moulded parts 13.

The afore-mentioned arrangement is then available as a so-called "instrument kit".

As shown in FIG. 3, the handgrip 21 can be screwed or pressed onto the proximal end of the rod-like portion 20 of the handle part 11.

All the features disclosed in the application documents are claimed as being of inventive significance, provided, they are novel over the prior art individually or in combination.

REFERENCE NUMERALS 10 setting instrument
11 handle part
12 suction element
13 flexible moulded part
14 pulling screw
15 threaded shank
16 screw head
17 internal thread
18 support flange
19 mounting or guiding sleeve
20 rod-like portion
21 handgrip
22 peripheral rim

The invention claimed is:

1. Instrument for handling a joint component of a joint prosthesis, which joint component comprises a joint surface, the instrument having a handle part and a suction element that can be brought into sealing contact with the joint surface, wherein the suction element comprises a flexible molded part configured to match to the joint surface, which molded part is deformable by a pulling element in such a way that, when applied to the joint surface, an increased partial vacuum is formed between the joint surface and the flexible molded part.

2. Instrument according to claim 1, wherein the pulling element is manipulable from the handle part.

3. Instrument according to claim 1, wherein the flexible molded part has a hemispherical suction portion.

4. Instrument according to claim 3, wherein the pulling element comprises a pulling screw having a threaded shank and a screw head, which in the case of the hemispherical suction portion of the flexible molded part is associated with the pole thereof.

5. Instrument according to claim 4, wherein the threaded shank of the pulling screw is arranged to be screwed into the distal end of the handle part, the flexible molded part then being clamped between the screw head and the handle part, or rather a support surface arranged at the distal end thereof.

6. Instrument according to claim 1, wherein the handle part has a rod-like portion against the distal end of which the flexible molded part is supported and the proximal end of which comprises a handgrip.

7. Instrument according to claim 6, wherein the rod-like portion of the handle part is either rigid or, at least in some regions, resiliently flexible.

8. Instrument according to claim 1, wherein the flexible molded part has a peripheral rim extending equatorially and radially outwards.

9. Instrument according to claim 1, wherein at the distal end of the handle part there is arranged, especially mounted so as to be rotatable relative thereto, a support flange against which the flexible molded part is supportable.

10. Instrument according to claim 9, wherein the support flange extends at least in part over the proximal surface of the flexible molded part.

11. Instrument according to claim 1, wherein the pulling element is non-rotatably anchored on the flexible molded part.

12. Instrument according to claim 11, wherein the pulling element is cast in the flexible molded part.

13. Instrument according to claim 1, wherein the pulling element is coupled to an actuating means, arranged on the handle part.

14. Instrument according to claim 1, wherein the flexible molded part is made of silicone or like material.

15. An instrument according to claim 13, wherein the actuating means comprises an actuating lever having an eccentric.

16. Instrument for handling a joint component of a joint prosthesis, comprising: a handle part and a suction element that can be brought into sealing contact with the joint component, the suction element comprises a flexible molded part configured to match a shape of the joint surface, the molded part is deformable by a pulling element in such a way that, when applied to the joint component, an increased partial vacuum is formed between the joint component and the flexible molded part, the pulling element comprises a pulling screw having a threaded shank and a screw head, the threaded shank of the pulling screw is arranged to be screwed into the distal end of the handle part, the flexible molded part then being clamped between the screw head and the handle part, and at a distal end of the handle part there is arranged a support flange against which the flexible molded part is supportable.

17. An instrument for handling a joint component of a joint prosthesis, the instrument comprising:
a handle, the handle having a proximal end portion and a distal end portion; a support flange connected to the handle at the distal end portion;
a suction element having a first side and a second side, the first side in contact with the support flange and the second side comprising a hemispherical suction portion shaped to correspond to a concave joint surface; and
a pulling element engaged with the suction element and operatively connected to the handle, wherein movement of the handle moves the pulling element which acts upon the suction element in such a way that an increased partial vacuum is formed between the second side of the suction element and the joint component when the suction element is in contact with the joint component.

18. The instrument of claim 1, wherein the pulling element is configured to apply a variable partial vacuum between the joint surface and the flexible molded part.

* * * * *